United States Patent [19]

Smit et al.

[11] 4,292,971
[45] Oct. 6, 1981

[54] ACNE SKIN TREATMENT APPLIANCE AND METHOD

[76] Inventors: Helen Smit; Julie Smit, both of 1045 Hinman Ave., Evanston, Ill. 60202

[21] Appl. No.: 64,730

[22] Filed: Aug. 8, 1979

Related U.S. Application Data

[63] Continuation-in-part of Ser. No. 801,850, May 31, 1977, Pat. No. 4,182,329.

[51] Int. Cl.³ .............................................. A61M 1/00
[52] U.S. Cl. ................................... 128/256; 128/276; 128/367
[58] Field of Search ................... 128/200.14, 276–278, 128/255, 367, 420

[56] References Cited

U.S. PATENT DOCUMENTS

| | | | |
|---|---|---|---|
| Re. 28,405 | 5/1975 | Sollerud | 128/276 |
| 1,965,424 | 7/1934 | Mascolo | 128/256 |
| 1,982,905 | 12/1934 | Davis | 128/256 |
| 3,749,092 | 7/1973 | Williams | 128/256 |
| 4,114,022 | 9/1978 | Braulke | 128/256 |
| 4,182,329 | 1/1980 | Smit et al. | 128/256 |

*Primary Examiner*—Norman Yudkoff
*Attorney, Agent, or Firm*—J. Warren Whitesel; Charles Laff; Larry Saret

[57] ABSTRACT

A personal appliance comprises a vacuum chamber and a steam-generating chamber. Steam or other heat is applied to an area of human skin for a period which is long enough to open pores, melt any wax-like substances within the pores, and otherwise cause the skin to be cleaned. Thereafter, a mild suction is applied to the steamed area which lifts the softened debris out of the open skin pores. In some instances the suction may be applied in a pulsating manner to massage the skin.

11 Claims, 11 Drawing Figures

U.S. Patent    Oct. 6, 1981    Sheet 1 of 2    4,292,971
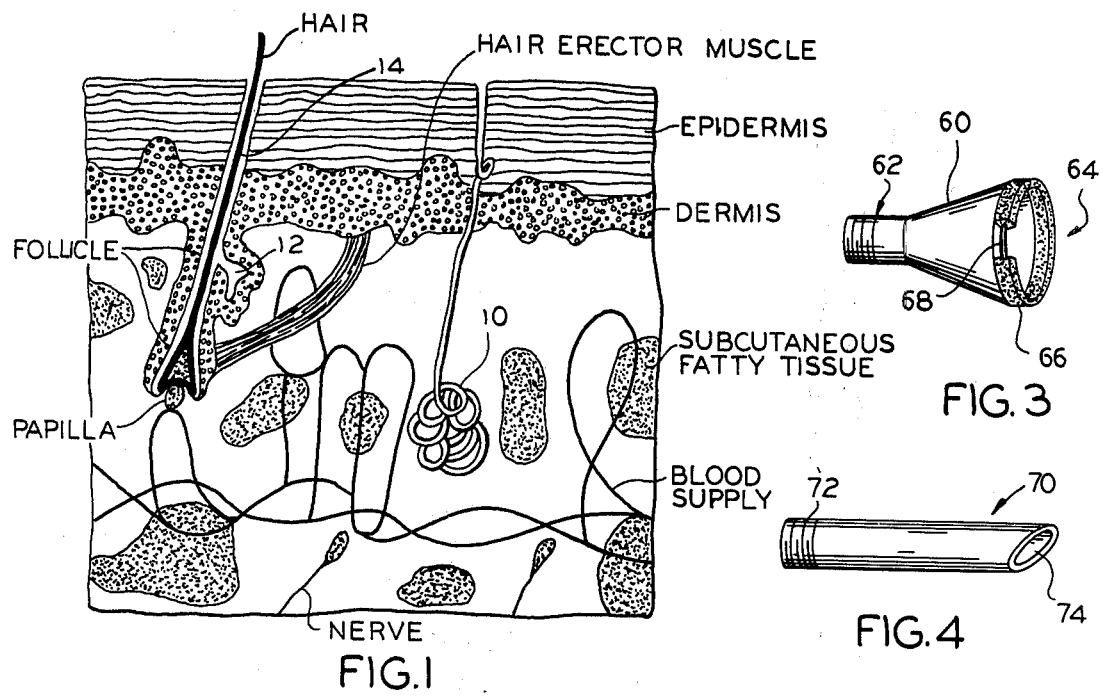
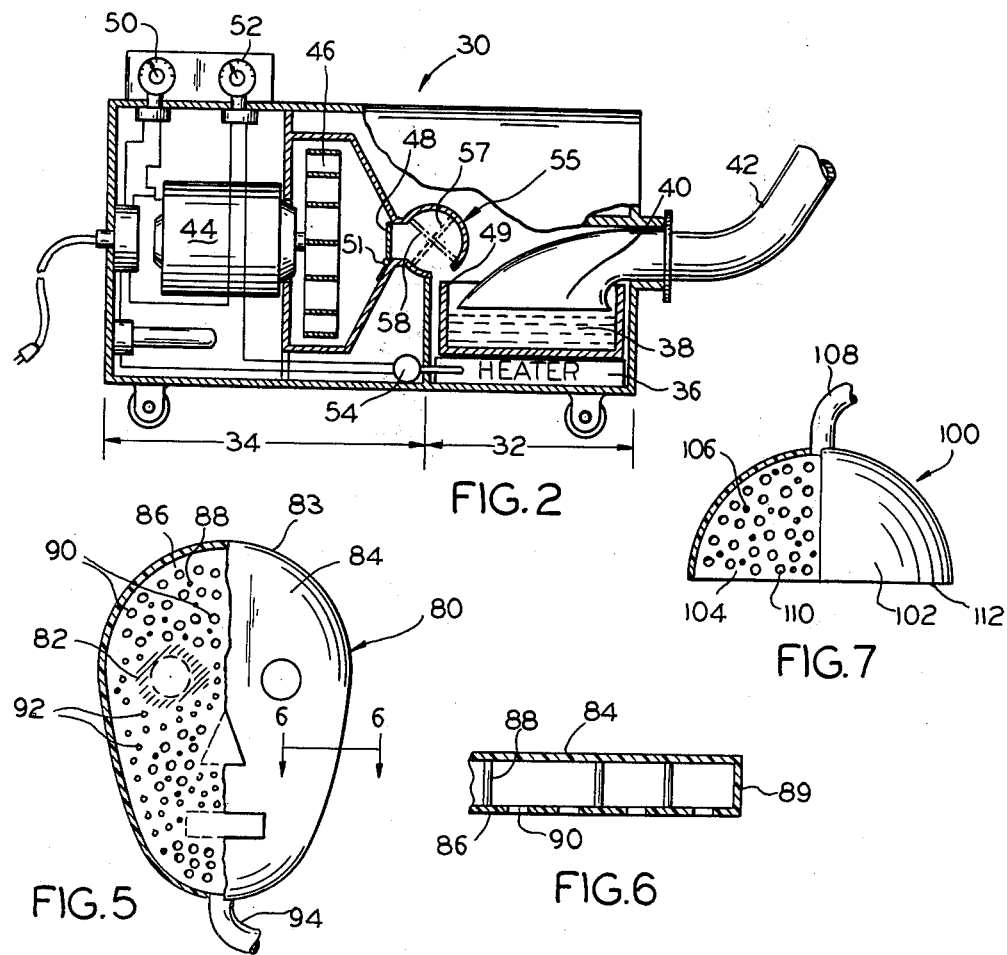

ACNE SKIN TREATMENT APPLIANCE AND METHOD

This is a continuation-in-part of our co-pending U.S. patent application Ser. No. 801,850, filed May 31, 1977, now U.S. Pat. No. 4,182,329.

This invention relates to skin treatments combining heat (especially a sauna bath type of treatment) for softening hardened oil in and opening the pores of human skin areas, and thereafter using a suction device for cleaning away the softened oil while the pores remain open.

Reference is made to a book entitled "Your Skin," by Margaret O. Hyde, McGraw-Hill, publisher, which describes acne as one of the more common human skin ailments. Most persons suffer from some degree of acne during their teenage years, and some continue to face the problems into their adult lives. The usual reason for this teenage affliction is that, during the sexual development of adolescense, the endocrine activity of the glands increases. These endocrine glands affect various parts of the body, including the sebaceous glands of the skin. The oily material, sebum, which these glands produce, tends to collect, harden and clog pores to produce acne.

Actually, the word "acne" encompasses a number of variations and diseases, each with its own characteristics. Basically, acne may take the form of blackheads, whiteheads, pustules, and sometimes deeper boil-like irritations. These blemishes occur most commonly on the face, and sometimes on the neck, shoulders, or chest. Acne is most important for its psychological effects, since it detracts from one's appearance, and may lead to severe and permanent scarring.

Dermatologists usually try to cure acne internally by giving drugs to the patient. With these treatments, it still takes six months or so to clear up even a mild case of acne. While these drugs work on preventing further outbreaks of acne, they do little to clear the existing acne.

Accordingly, an object of the invention is to provide new and improved means for and methods of immediately improving the appearance of a person having acne by cleaning out clogged pores.

Yet another object is to make a patient's skin look better, so that he will be less apt to worry about it, since worrying often produces more oil which, in turn, clogs more pores and exacerbates the acne.

Still another object of the invention is to provide new and improved means for and methods of deeply cleaning human skin.

In keeping with an aspect of the invention, these and other objects are accomplished by providing heat, such as a steam or sauna type of bath, which opens pores, softens hardened oils and tends to cause the softened oils to drain from the pores. Once the pores begin to drain properly, a suction source draws the oils away from the face. If desired, the suction may be applied in a pulsating manner to massage the skin.

The appended drawings show preferred embodiments of the invention, wherein:

FIG. 1 schematically shows a cross section of human skin and tissue to illustrate how and why acne occurs;

FIG. 2 schematically shows one embodiment of a personal appliance incorporating the invention;

FIG. 3 shows a large area treatment attachment for use with the appliance of FIG. 2;

FIG. 4 shows a small area treatment attachment for use with the appliance of FIG. 2;

FIG. 5 shows a facial mask appliance attachment for use with the appliance of FIG. 2;

FIG. 6 shows a fragmentary cross section of the facial mask of FIG. 5;

FIG. 7 shows a scalp treatment attachment for use with the appliance of FIG. 2;

Figure 8:
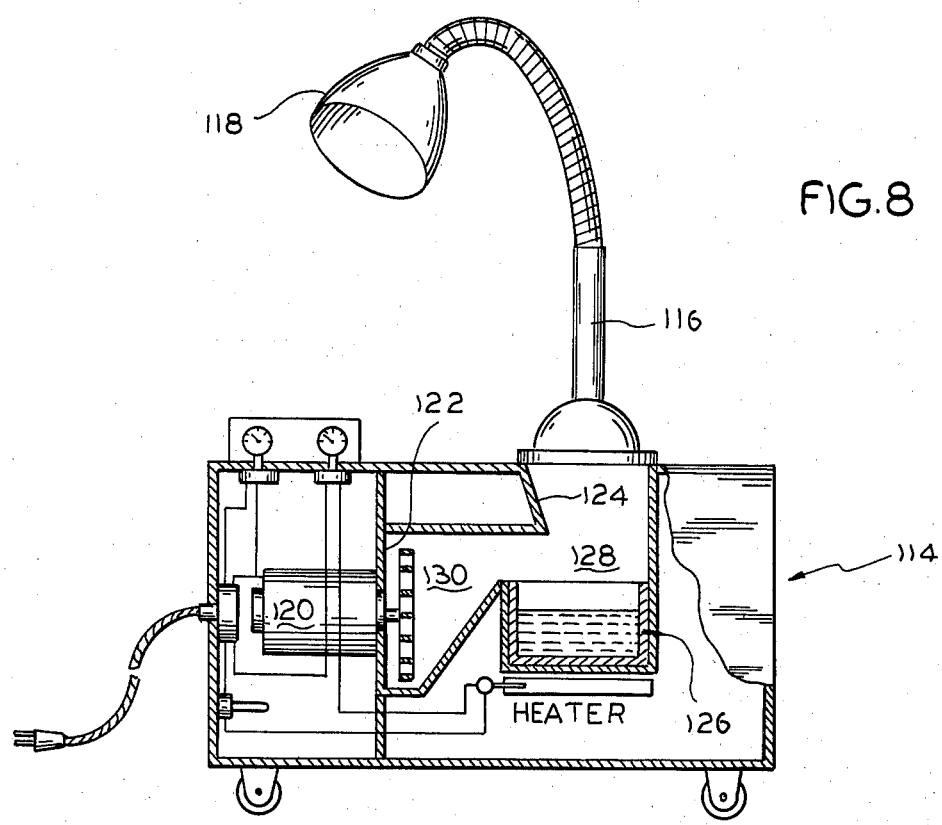
Figure 9:
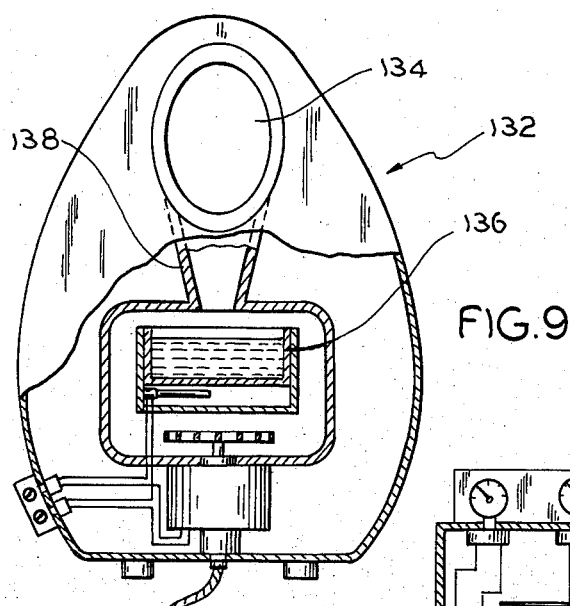
Figure 11:
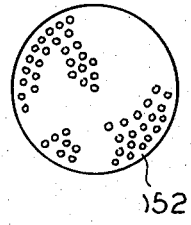
Figure 10:
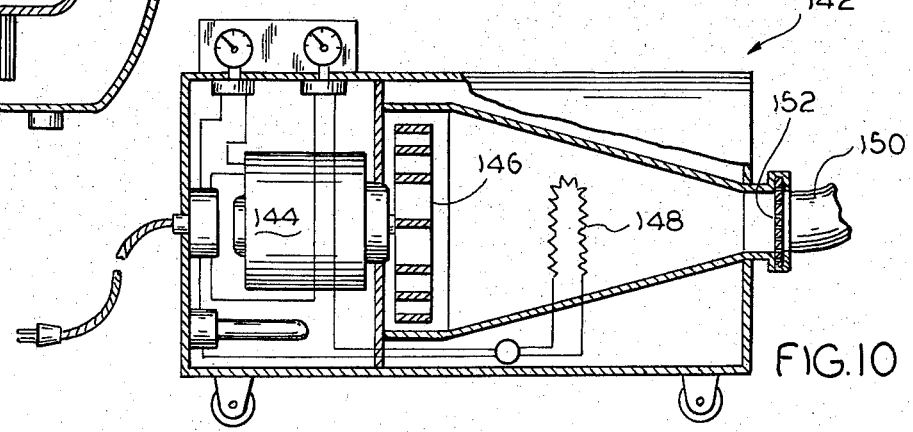

FIG. 8 schematically shows a second embodiment of the inventive appliance in a table or floor stand version;

FIG. 9 shows a third embodiment sauna/suction appliance, which does not utilize attachments;

FIG. 10 shows a fourth embodiment with an alternate means for heating a skin area before suction is applied; and FIG. 11 shows a porous filter for collecting sucked-in debris.

As seen in FIG. 1, two sets of glands (the sweat gland 10 and the sebaceous (oil) glands 12) discharge their secretions over the skin. The sebaceous glands' oily secretion, sebum, normally lubricates the skin, keeping it moist and flexible. The sebaceous glands are most numerous on the forehead, chin, and around the nose. When a sebaceous gland becomes overactive, the oil hardens within the duct 14 leading to the surface of the skin. This hardening of the oil causes the duct to expand, which tends to stretch the pore opening, thereby causing it to contract. Then, the pore becomes clogged and plugged up. Therefore, to treat this acne condition, the pore needs to be reopened and the hardened oil needs to be softened. This can be done by heating the skin area containing the clogged pore. Since heat expands and melts oils and waxes, this steam expands the pore openings and softens the oils. However, heating alone does not automatically improve acne because, if the oil remains in the duct 14, it will likely reharden within a short time after the heat is removed. Therefore, the invention preferably contemplates applying a suction to the pore during and directly after a steaming process. The suction removes the liquefied oil, leaving the duct clear, and enabling it to return to normal. However, the sequence and timing of the steaming and vacuuming may vary from person to person.

The inventive personal appliance 30 includes two parts forming a sauna-forming chamber 32 (FIG. 2) and a vacuum-forming chamber 34. The sauna chamber 32 comprises a heating element 36, a removable water and waste collector tray 38, and a steam-collecting hood 40 positioned over tray 38 and leading to hose 42. The vacuum-forming chamber 34 includes a reversible motor 44 and impeller 46. A spring-biased valve 48 normally closes the vacuum-forming chamber 34 from the sauna chamber 32. Normally, the motor runs in one direction to draw a vacuum; however, it may also be run in an opposite direction to blow warm and moist air up the hose 42, in which case, the valve 48 must be opened against the bias of spring 51.

The hood 40 is a down-draft filter positioned above and very near the surface of water in the tray 38, but not so close that it would reduce or interfere with the draft of air drawn into a vacuum chamber. The baffle 49, at the back of the water tray 38, raises high enough above the surface of the water to interfere with any heavy particles in the air stream. Therefore, when the vacuum is drawing air through the hose 42, the light gas atoms will be sucked from hose 42 into the vacuum chamber. However, any heavier particles will have considerable inertia, will continue on a downward path from the hose 42, and will be entrapped by the water.

Any suitable switches 50,52 may be provided, individually and respectively, to control the vacuum 34 and the sauna chamber 32. Each of these switches may be adapted to provide a range of settings extending from "off" through "low" and "medium" to "high." The sauna chamber control switch 52 is connected through a thermostat 54 to heating element 36 to maintain a heating level which is selected by the switch 52.

Depending upon the setting of switch 52, the heating element 36 increases the temperature of the water in tray 38. At a high temperature, the water is vaporized into steam. Positioned above the water 38 is a vapor-collecting hood 40 which receives and collects moisture and heated air that is rising from the water 38. The convection currents generated by the rising stream of hot air pass through the hose 42.

Interposed between the vacuum and sauna chambers may be a rotating valve 55 for causing a pulsation of either warm or moist air which is blown over the skin or vacuum which draws the softened material from the skin. In greater detail, as schematically drawn, a rotor in valve 55 may be in position 57 to block the flow of air or other gas between chambers 32,34. Or, the rotor may be in position 58 to enable such a flow. If the rotor is rotating, the flow of gas is pulsating. The speed of rotation may be varied according to personal needs.

The hose is terminated by any one of many attachments which is held near the face or other body part of a person who is using the vacuum device. The attachments are detachable so that they may be washed. In greater detail, FIG. 3 shows a flaring or a funnel-shaped attachment 60 which is flexible and can fit, at its end 62, on to the end of the hose 42. The outer end 64 of the funnel 60 terminates in a sponge material 66, here shown partially in cross section to illustrate a flexible, yet somewhat stiff, ring 68 embedded therein. The sponge will be slightly porous to the extent that ambient external air may brush over the face and enter the hose 42, when the vacuum is running. This ring 68 may be a steel spring, for example, which adapts itself to the contours of the face while it is held in position. Yet, when the attachment 60 is removed from the face, the spring returns to its normal position. The funnel-shaped attachment 60 may also be molded in the shape of and used for treating larger skin areas such as the forehead, cheeks, shoulders, back, and chest.

FIG. 4 shows another attachment 70 which may be made from a fairly rigid material, such as plastic or hard rubber, for example. The end 72 attaches to the hose 42. The end 74 fits a highly localized area which is small enough so that contoured fitting is not required. For example, the end may have an oval contour which is about $1'' \times \frac{1}{2}''$. This appliance is best used around the nose, hairline, or for individual blemishes.

Yet another attachment 80 is seen in FIG. 5, which is in the form of a facial mask. Preferably, the facial mask is moldable to conform to the contours of a face. While the contours may be in any convenient form, mask 80 is here shown as full-face mask having cutouts for eyes, nose and mouth. Preferably, each of these cutouts is surrounded on the underside of the mask by a suitable material for sealing against the skin. For example, the crosshatched area 82 indicates a location of a sponge rubber gasket which will prevent the steam or other heat and suction from reaching the right eye socket of a person wearing the mask. Facial mask 80 may have an elastic band for encircling the head and holding the mask against the face. Or, an elastic drawstring 83 may be incorporated around its outer circumference so the mask will fit in close contact with the facial area without requiring human assistance to hold it is place.

The facial mask 80 has an unbroken outer upper surface 84 and a perforated inner or lower surface 86 held in a spaced relationship by a number of posts or supports 88. These two surfaces are sealed together around all edges, as shown at 89 (FIG. 6). The perforations (one of which is numbered 90) are distributed over the inner surface according to the frequency with which acne occurs in that area. In areas where acne is most likely to occur, the perforations are large (as at 90) and in areas where it is less likely to occur, they are small (as at 92).

The facial mask is made from material which is sufficiently rigid so that the two sides will not collapse and come into contact with each other when they are supported in spaced relationship by posts 88. A hose 94 is integrally formed on the mask 80 to enable it to be connected to the hose 42. Thus, there are communication passages extending from the interior of appliance 30, through hoses 42,94, the space between upper and lower surfaces 84,86 and out the perforations 90,92.

To further illustrate that the mask may be adapted to fit any part of the body, FIG. 7 shows a skull cap attachment 100 which is adapted to fit over the top of the skull. This mask is constructed similarly to the mask of FIG. 5 and has a cross section similar to that shown in FIG. 6. Again, there are upper and lower (or outer and inner) surfaces 102,104 with supports 106 between them. Hose 108 provides a means for connecting the attachment 100 to the hose 42. Perforations 110 are formed in the lower surface 104 so that the moisture and vacuum may reach the skin of a person wearing the skull cap. The bottom 112 of the cap may terminate in an elastic band which seals the skullcap to the head.

The operation of the device should now be clear. An appropriate attachment is placed upon the end of hose 42. The heating element 36 is energized to vaporize the water in tray 38. As the selected attachment is held against the face, steam rises through the hose and to the face. For example, if the funnel 60 is held against a cheek, steam rises to warm and wet the cheek. If desired, the fan motor 44 may be reversed and driven at very low speed to drive the steam vapors toward the treated skin area. If so, the valve 48 may be opened manually.

After a suitable period of time, the area of the skin encompassed by the attachment will have been bathed in warm moisture-laden air long enough to open the pores and soften embedded wax-like deposits. Then, the vacuum is switched on for a period which is long enough to draw the water, oil or other material from the pores in the treated skin area. The treatment may be repeated periodically until the pores are cleaned out. If desired, the suction may be made to pulsate to further aid in removing the oil. The pulsation, if used, also massages a desired area of the skin.

The invention is not limited to treatment of acne, but may be used any time that it is either necessary to desirable to treat skin with heat or moisture or with a gentle pulsating suction.

For example, in a book by Carlson Wade, "The Natural Way to Beauty and Health" (New York: Bantam Books, 1968) p. 38–39, there is a case history of a man who was suffering from hair loss and who benefitted from massage and steam treatments. On the first day of the week, this man applied white iodine to his scalp with a swab of absorbent cotton. On the next day, he massaged the scalp with castor oil. He continued this alternate application of white iodine one day, castor oil and massage the next, etc. On the seventh day, he soaked a towel in hot water and wrapped it, steaming, around his head like a turban. He let it remain thirty minutes. He repeated this steaming process five times. Then, he shampooed his hair with castile soap. He did this one week every month and claimed that it not only stopped his hair loss but increased hair growth.

Apparently, it is thought that each hair grows from a tiny pocket or follicle in the scalp. In the bottom of this pocket or follicle is a little mound, the papilla, which is the root from which the hair grows. The papilla and the follicle are supplied with blood vessels. Growth of a hair takes place at the junction of the follicle and the papilla. The blood vessels bring cells to the papilla which pushes them up into the follicle where they harden and become a strand of hair. If true, it would appear that, by improving the scalp's circulation, balding people can bring more cells to the papilla which in turn may tend to produce hair.

We do not necessarily endorse this accounting by Carlson Wade. The point is that he, and many others, often prescribe heat or massage treatments calculated to bring blood to a surface of the skin. For many, if not most, of these prescriptions, the inventive device should bring added treatment.

FIG. 8 shows a second embodiment of the sauna/suction appliance. Appliance 114 does not have a pulsating means. It does have an upright, twistable and adjustable tube 116, replacing hose 42, with a funnel-shaped attachment 118 to point in a desired direction, fastened thereto. An advantage growing out of this use of tube 116 is that a person can sit and then adjust the attachment 118 to fit against a selected area of skin, and to be at a suitable height for treatment. The person may then sit in a comfortable position while receiving a skin treatment. Alternately, any of the attachments of FIG. 4, 5 and 7 may be used in place of funnel 118, if such other types of attachments are desired.

Appliance 114 may include a reversible motor 120 if it is desired to blow heat or steam to the skin area. However, the steam also rises through tube 116 and attachment 118, by its own convection currents, to treat a skin area. Therefore, the use of a reversible motor is primarily an option.

Motor 120 is sealed from sauna chamber 128 and vacuum chamber 130 by wall 122 so that the moisture of the sauna will not damage the motor. The sauna chamber and vacuum chamber are designed to prevent cool air from flowing into the passageway, which might cause the steam to condense and form water droplets. Sufficient heat is thus maintained in order to open the skin pores and melt the hardened oils within the pores.

FIG. 8 further replaces the down-draft hood 40 of FIG. 2 with a wall 124 which directs the vacuumed moisture and debris into a removable water tray 126. If desired, pulsating suction may also be incorporated into the appliance 114.

FIG. 9 shows a third embodiment of the sauna/suction appliance 132, which does not need attachments. Here, a person places the skin area to be treated over a window or opening 134. The steam rising from water tray 136 is directed on to the skin area held next to window opening 134. Thereafter, a suction is applied to the skin area held next to the window opening 134 and walls 138 direct the vacuumed moisture and debris into the removable water tray 136.

FIG. 10 shows yet another embodiment for applying heat to open skin pores and melt the hardened oil and debris within the pores before a suction is applied. In greater detail, appliance 142 contains a reversible motor 144. Impeller 146 blows air through a heated coil 148 and into hose 150 to treat a skin area with hot dry air. Any one of the attachments shown in FIG. 3, 4, 5 or 7 may be attached to the end of hose 150. Then, the motor may be reversed to apply suction to the skin area in order to remove the melted oil and debris from within the open skin pores. In the embodiment of FIG. 10, debris removed during the vacuuming step may be captured in a porous, mesh-type filter 152 (FIG. 11) which may be situated within hose 150 or elsewhere, as in the attachment, for example. If desired, a pulsating suction may also be incorporated into this embodiment, although it is not shown.

There are still other ways to accomplish our method for treating acne by application of heat and suction. Another such method involves an application of a chemical solution to the skin, such a chemical including a combination of a weak acid and a weak base to form heat, such as vinegar and a weak ammonia solution or alcohol and water. The two chemicals interact to form heat which opens the skin pores and softens the debris solidified within the follicles. Then, a suction is applied to the skin area, to remove the softened debris.

Our method of cleaning skin pores, for the treatment of acne, could also be accomplished with many other suitable heating sources, before a suction is applied. Furthermore, there are many different combinations for the structure disclosed herein. For example, the appliances could be a hand-held device (similar to hand-held blow dryers) used for an application of heat followed by a suction.

Also, both blowing and suction could be derived from a standard motor if two passageways are used on opposite sides of the impeller. One passageway leads to the front of the impeller for blowing the heat on to the skin and the other passageway leads to the back of the impeller for sucking debris from the skin area.

Therefore, the appended claims are to be construed broadly enough to cover all equivalent structures and methods falling within the true scope and spirit of this invention.

We claim:

1. Apparatus for treating human skin, said apparatus comprising heater means for producing a draft of heated air directed against an area of skin, the heat of said air being sufficient to cause a physical change to occur within the pores of the heated skin without damage to said skin, said heater means being disposed within a passageway which is in direct communication with said area of skin to be heated in order to direct the heat directly on to only said area of skin, said passageway guarding said draft of air to prevent an ambient cooling thereof and to prevent any change of state of the heated air within said passageway, said physical change in said pores being an enlargement of their openings and a melting and softening of solidified debris within a follicle in said pore respective to said heated air, vacuum-producing means for applying an air suction through said passageway to said area of skin to draw the melted and softened debris out of the enlarged skin pores, said removed debris being drawn by said vacuum-producing means from said heated area of skin through said passageway and into means for collecting said removed debris, said last-named means being removable so that it may be washed and cleaned, the apparatus further comprising a motor chamber sealed and separated from the sauna chamber by a vertical wall, an air directing conduit extending from the wall to the water container within the sauna chamber, the said conduit formed by an upper horizontal wall and a lower inclined wall to define a tapering air path in the direction toward the water container, a blower positioned within the conduit at the wider extremity of the taper, the said closed passageway extending from the steaming area being provided with a funnel stream applicator at its extremity with a smaller dimension of the funneel secured to the passageway and the wider dimension having a sponge material around its peripheral circumference.

2. The apparatus of claim 1 wherein said heater means comprises a container for water and means for boiling said water to create steam, said means for preventing a change of state of said heated air including means for preventing said steam from condensing into water droplets before reaching said heated area of skin.

3. The apparatus of claim 2 and means for carrying said steam to said heated area of skin by convection currents.

4. The apparatus of claim 2 wherein said heater means, said vacuum-producing means and said passageway are part of a common appliance within a single housing.

5. The apparatus of claim 1 wherein said heater means comprises a heater for dry air and said means for preventing a change of state of said heated air comprises means for preventing an introduction of ambient air which may add moisture to said dry air.

6. The apparatus of claim 1 wherein said suction-applying means comprises a reversible motor, said motor operating in one direction for driving said heated draft toward said skin area and operating in an opposite direction for vacuuming waste from said heated skin area, the impeller on said reversible motor being situated within a housing having a continuous passageway leading to said skin area, wherein said passageway is one conduit used for both driving said heated draft toward the skin area and vacuuming waste from said skin area.

7. The apparatus of claim 6 and valve means for selectively controlling the direction of air flow toward or away from said skin area.

8. The apparatus of claim 1 and valve means for selectively controlling the direction of air flow toward or away from said skin area.

9. The apparatus of claim 1 wherein said collection means is a filter situated at a location where said debris collects.

10. The apparatus of claim 1 wherein said collection means is a removable water tray situated at location where said debris collects.

11. The apparatus of claim 1 wherein said apparatus comprising a housing having an opening with internal walls extending from said opening to both said heat source and said vacuum-producing means whereby said opening may be used to treat said area of skin without requiring separate attachments.

* * * * *

UNITED STATES PATENT AND TRADEMARK OFFICE
CERTIFICATE OF CORRECTION

PATENT NO. : 4,292,971

DATED : October 6, 1981

INVENTOR(S) : Smit, et al.

It is certified that error appears in the above—identified patent and that said Letters Patent is hereby corrected as shown below:

Col. 4, Line 61, "to" should be --or--;

Col. 6, Line 63, "respective" should be --responsive--;

Col. 7, Line 14, "funneel" should be --funnel--.

Signed and Sealed this

Second Day of March 1982

[SEAL]

Attest:

GERALD J. MOSSINGHOFF

Attesting Officer

Commissioner of Patents and Trademarks